Feb. 16, 1965 H. KERRIGAN Plant Pat. 2,471
AZALEA PLANT
Filed Dec. 27, 1963
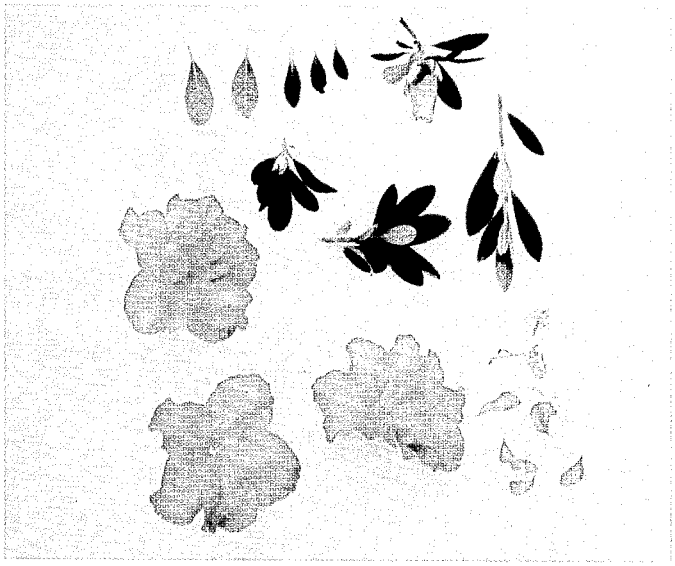
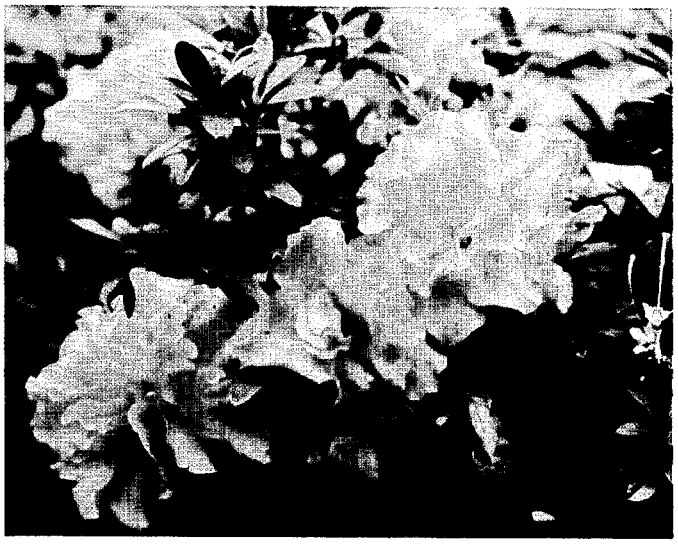

United States Patent Office

Plant Pat. 2,471
Patented Feb. 16, 1965

2,471
AZALEA PLANT

Howard Kerrigan, 3003 Totterdell St., Oakland, Calif.

Filed Dec. 27, 1963, Ser. No. 334,064
1 Claim. (Cl. Plt.—57)

This disclosure concerns a new and distinct variety of azalea plant of the florists' forcing type developed by me at Oakland, California, in 1952 as a direct result of a breeding program initiated by me in 1943 and carried out by me at Oakland, California.

The main objective of this particular phase of said breeding effort was the production of a deep blood red, early, forcing azalea of the Belgian Indica type but with an increased color stability and flower life on the finished plant than presently exists in Belgian Indica forcing azaleas in the red color range, and a plant of improved vigor and habit.

This objective was achieved by crossing the variety Mme. Charles Vuylsteke (unpatented), the seed parent, with the variety L. C. Bobbink (Plant Pat. 611), the pollen parent.

My new variety excels both its parents, which are presently the leading varieties of their type and color range, in vigor, color, growth, life of the bloom, and rate of growth. Particularly important is the glowing blood red color that lasts throughout the life of the flower and the fact that the flowers remain on the plant for an unusually long time.

All of these characteristics have proven fixed and stable through numerous generations of asexually produced plants propagated by me from own root cuttings at Oakland, California, since 1955.

The accompanying drawings disclose those details of my new variety of azalea plant that may be effectively disclosed in this manner. These drawings show the colors of the foliage and flowers substantially as they appear in nature and as accurately as current methods will allow. Several anatomical and morphological details are also illustrated in the drawings.

The following horticultural and botanical descriptions of my new azalea plant further disclose and reveal the new and distinct features of this invention. The color designations employed are those used in the Horticultural Colour Chart issued by Wilson Colour Ltd. in collaboration with the Royal Horticultural Society.

*Horticultural description*

Vigorous, compact, heavily branched, rounded shrub of medium size, reaching about 20 inches at maturity. The foliage is slightly shiny. The leaves are of medium size, widest beyond their middles, 1 11/16 inches long by ½ inch wide. The young stems are reddish with considerable white, wooly hairs. The older stems appear tan because of the abundance of long flat tan persistent hairs. The leaves are dark green (Ivy Green, HCC 0001060/3) on the upper surface and light green (Spinach Green, HCC 0960/3) on the lower surface. The young foliage is much lighter than the mature and takes more time to darken than most varieties. The pubescence of the leaves is black and conspicuous. The leaf blade is 1 7/16 inches long and slightly rolled under at the base.

The flower is double. The calyx is normal. The sepals are unequal in size, green except for a reddish triangular marking at their bases, with rounded feathered tips.

The corolla is Currant Red (HCC 821/1), broadly flaring, ¾ inch deep and 3¼ inches across. The tube is short, being only ⅝ inch deep. The lobes of the corolla are broad, essentially circular in outline, the edges of the lobes are wavy. The lobes are of two sizes. The upper three measure about 1¼ inches long by 1 5/16 inches wide while the lower two measure about 1⅜ inches in both directions. The upper lobes and the front part of the throat are marked Chrysanthemum Crimson (HCC 824/1).

Normal stamens are few or missing altogether. In many flowers two whorls of stamens are modified into a super hose of varying degrees of perfection. This hose is usually fluted and grooved and gives the center of the flower a distinct ruffled appearance. This staminal hose has from 7–10 lobes which measure 1⅛ inches in both directions. Within the staminal hose there are ordinarily a number of petaloids sometimes free but more often variously fused along their lower edges to the inner staminal hose and to the ovary. Occasional stamens with normal filaments occur. These are about ⅞ inch long and Currant Red. The anthers are also Currant Red, about 1/16 inch long.

The pistil is usually deformed. There are usually a number of supernumary styles fused in varying degrees and of varying lengths so that extra stigmas are present at many distances from the ovary. The stigma then is compound and scattered. The style is essentially straight in these flowers. Occasional normal pistils are produced.

This variety has proven to be completely sterile.

*Botanical description*

Rounded, compact shrub to 20 inches, usually somewhat taller than wide but barely so. Stems reddish when young with white wooly pubescence which becomes tan, long lanceolate strigae on the older stem. The mature pubescence completely clothes the shoots. The foliage is medium sized, 1 11/16 inches long by ½ inch wide, oblanceolate, petiolate, the petiole 5/16 inch long, the blade is dark green above, light green below, 1 7/16 inches long. The leaf margin is entire, ciliate. The leaf apex is bluntly mucronate. Pubescence of the leaf is black and conspicuous, flattened and long lanceolate. The lamina is slightly decurrent and the proximal margins rolled slightly downward.

The terminal flowering buds are large, 5/16 inch long by 3/16 inch wide. The scales where exposed are covered with dark pubescence distally. The inflorescence bears 3–4 flowers each.

The pedicel is ⅜ inch long, reddish and stout. The calyx is light green, irregular, ciliate to fimbriate, especially at the apex. The sepals are light green with a triangular reddish marking proximally and a nearly white base. The sepals are sub-linear with a rounded apex. The three dorsal lobes of the calyx are conspicuously smaller than the ventral two.

The corolla is Currant Red, very broadly flaring, 3¼ inches wide and ¾ inch deep. The tube is short, 1 inch across and ⅝ inch deep, very abruptly flared from the receptacle. The limbs of the corolla are large, showy, strongly auriculate, undulate and irregular. The dorsal three are 1¼ inches long and 1 5/16 inches wide. The ventral two are 1⅜ inches long by 1⅜ inches wide. The proximal portion of the dorsal limbs and the distal portion of the throat are spotted Chrysanthemum Crimson.

Stamens are few or none. A second hose of staminal origin is usually well developed. This hose is grooved and pleated, with 7–10 lobes, the lobes are imbricate. Petaloids ordinarily occur within the staminal hose. The petaloids are Currant Red as is the staminal hose and the dorsal staminodes and the dorsal portion of the staminal tube are marked with dark crimson as is the corolla. The petaloids are variously fused along their bases and variously adnate to the staminal hose and the ovary. Morphologically normal stamens occur. These are short, ⅞ inch long, Currant Red throughout. The anthers are 1/16 inch long.

The pistil is 1¼ inches long. The style is deformed in most flowers, highly fasciated, with many supernumary styles and stigmas variously fused or free. The style is very stout and essentially straight when of this type. Normal styles are seen but these are rare. When normal, the style is slender, of uniform diameter and slightly sigmoid. The color of the style is Currant Red. The base of the style, especially those few normal ones, bears patent stiff setae on the proximal third of their length.

All efforts to use this variety as a parent have failed. It is apparently sterile both as a seed parent and a pollen parent.

Having disclosed my new invention in the above descriptions and in the accompanying drawings, what I claim as new and patentable is:

A new and distinct variety of forcing azalea of the Belgian Indica type characterized primarily by its extremely deep rich color, which is Currant Red, by its exceptionally large flower size, by its ability to retain its opened flowers on the plant for a long period of time under florists' use conditions, by its retention of its rich red color when forced and throughout the life of the flower, by its ease of propagation from cutting, by its compact habit of growth and its strong, vigorous growth.

No references cited.

ABRAHAM G. STONE, *Primary Examiner.*